United States Patent
Sampson

(10) Patent No.: US 7,905,862 B2
(45) Date of Patent: Mar. 15, 2011

(54) METHOD AND SYSTEM FOR DRUG DELIVERY

(75) Inventor: Russel M. Sampson, Palo Alto, CA (US)

(73) Assignee: Cytyc Corporation, Marlboro, MA (US)

( * ) Notice: Subject to any disclaimer, the term of this patent is extended or adjusted under 35 U.S.C. 154(b) by 756 days.

(21) Appl. No.: 11/735,921

(22) Filed: Apr. 16, 2007

(65) Prior Publication Data
US 2007/0185435 A1    Aug. 9, 2007

Related U.S. Application Data

(62) Division of application No. 11/280,979, filed on Nov. 15, 2005, now abandoned.

(60) Provisional application No. 60/627,684, filed on Nov. 15, 2004.

(51) Int. Cl.
*A61M 5/178* (2006.01)

(52) U.S. Cl. .................................. 604/164.01; 600/101

(58) Field of Classification Search ................ 604/158, 604/164.01, 164.06, 164.07; 600/135, 101, 600/104
See application file for complete search history.

(56) References Cited

U.S. PATENT DOCUMENTS

| | | |
|---|---|---|
| 3,995,629 A | 12/1976 | Patel et al. |
| 4,900,303 A | 2/1990 | Lemelson et al. |
| 5,261,889 A * | 11/1993 | Laine et al. ............. 604/164.11 |
| 5,380,292 A | 1/1995 | Wilson |
| 5,618,268 A * | 4/1997 | Raines et al. .................. 604/82 |
| 5,702,344 A | 12/1997 | Silverstein et al. |
| 5,997,509 A | 12/1999 | Rosengart et al. |
| 6,059,766 A | 5/2000 | Greff et al. |
| 6,296,608 B1 | 10/2001 | Daniels et al. |
| 6,425,854 B1 | 7/2002 | Galt et al. |
| 6,461,296 B1 | 10/2002 | Desai |
| 6,471,678 B1 * | 10/2002 | Alvarez de Toledo et al. .................................. 604/264 |
| 6,582,441 B1 | 6/2003 | He et al. |
| 6,758,806 B2 * | 7/2004 | Kamrava et al. ............. 600/153 |
| 7,044,934 B2 | 5/2006 | Mickley |
| 7,087,040 B2 | 8/2006 | McGuckin, Jr. et al. |

OTHER PUBLICATIONS

International Search Report and Written Opinion of the International Searching Authority, PCT Application Serial No. PCT/US2005/041995, Mar. 15, 2006, 16 pp.

* cited by examiner

*Primary Examiner* — Theodore J Stigell
(74) *Attorney, Agent, or Firm* — Lindsay McGuinness

(57) ABSTRACT

A medical device and procedure for delivering a drug into a uterus are described. In one implementation, the medical device includes a first elongate member, a second elongate member and a stopper device. The first elongate member is configured for transcervical insertion into the uterus and includes a lumen extending therethrough. The second elongate member is positioned within said lumen and also includes a lumen therethrough. The second elongate member is positionable in a retracted or an extended position. A distal end of the second elongate member is configured to extend beyond a distal end of the first elongate member and penetrate uterine tissue when in the extended position. A proximal end of the second elongate member is configured to receive a drug for delivery through the lumen of the second elongate member. The stopper device controls movement of the second elongate member within the first elongate member.

10 Claims, 4 Drawing Sheets

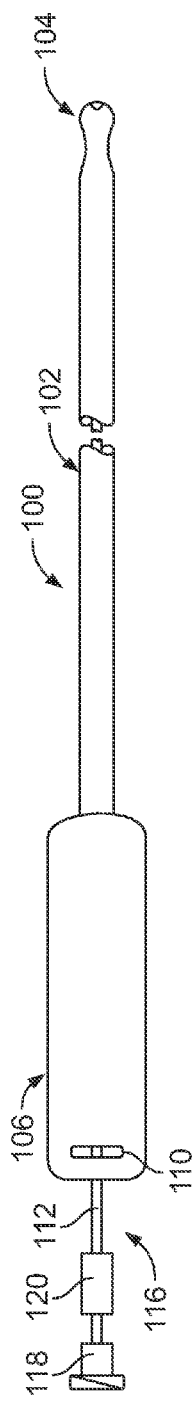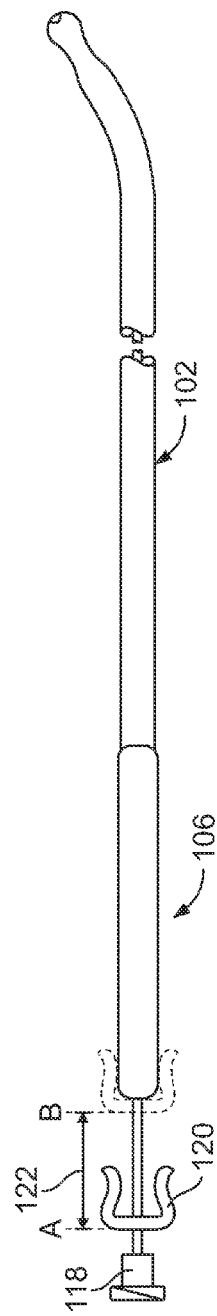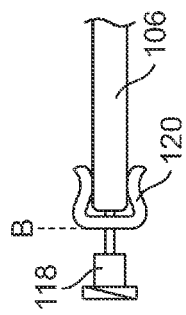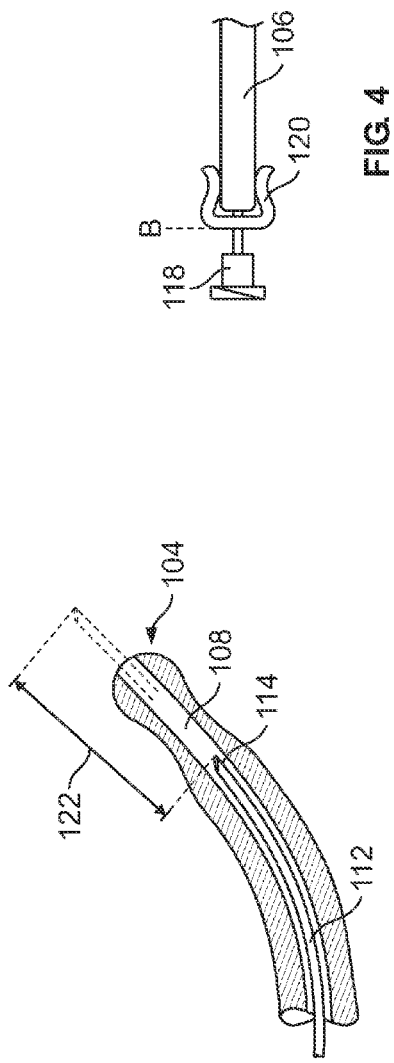
FIG. 1
FIG. 2
FIG. 4
FIG. 3

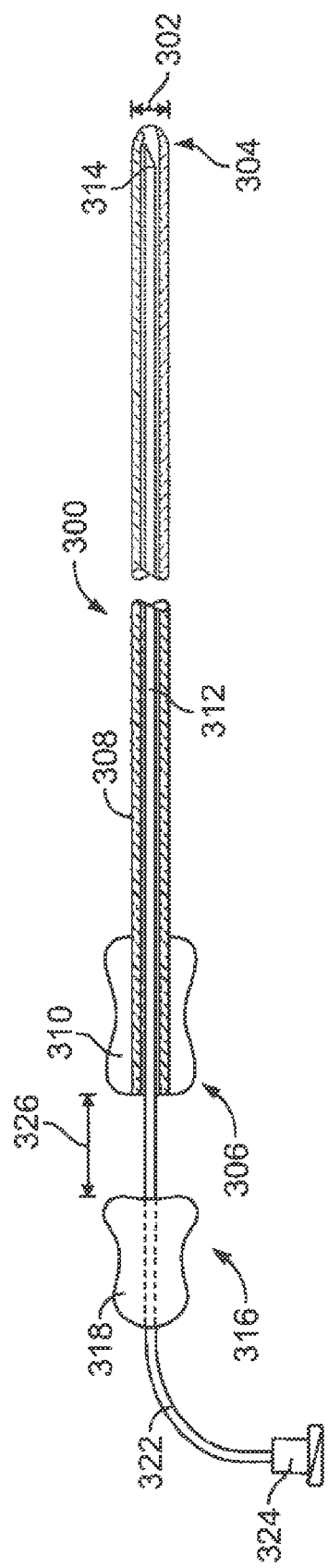
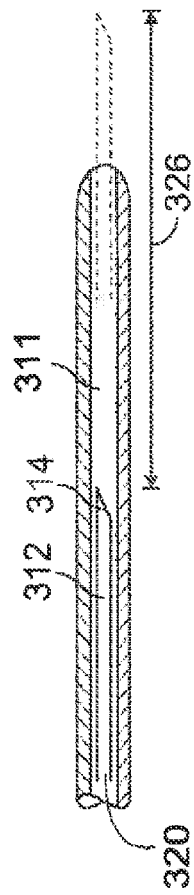
FIG. 6
FIG. 7

METHOD AND SYSTEM FOR DRUG DELIVERY

CROSS REFERENCE TO RELATED APPLICATIONS

This application is a divisional of and claims priority to U.S. application Ser. No. 11/280,979, entitled "Method and System for Drug Delivery", filed on Nov. 15, 2005, now abandoned, which claims priority to U.S. Provisional Application Ser. No. 60/627,684, entitled "Method and Apparatus for Local Anesthesia Delivery", filed on Nov. 15, 2004, both of which are hereby incorporated by reference in their entireties as part of the present disclosure.

TECHNICAL FIELD

This invention relates to a medical device and procedure.

BACKGROUND

Endometrial ablation and other transcervical procedures have historically been performed in an ASC (Ambulatory Surgery Center) or hospital operating room setting, where intravenous sedation or general anesthesia is readily available. As medical procedures migrate to the physician's office, these forms of sedation are less desirable. A local anesthesia is most desirable, since no anesthesiologist is needed. However, with respect to transcervical procedures, a para-cervical block (PCB) or intra-cervical block (ICB) can adequately anesthetize the cervix and most of the uterine corpus, but typically does not reach the fundus of the uterus. Various formulations of topical anesthetics have been instilled into the uterine cavity, but their absorption, for example into the endomyometrial tissue, can be inadequate.

SUMMARY

This invention relates to a medical device and procedure. In general, in one aspect, the invention features a medical device for drug delivery. The medical device includes a first elongate member, a second elongate member and a stopper device. The first elongate member is configured for transcervical insertion into a uterine cavity and includes a proximal end, a distal end and a lumen extending therethrough. The second elongate member is positioned within the lumen of the first elongate member and includes a proximal end, a distal end and lumen therethrough. The second elongate member is positionable in a retracted or an extended position relative to the first elongate member. The distal end of the second elongate member is configured to extend beyond the distal end of the first elongate member and penetrate uterine tissue when in the extended position. The proximal end of the second elongate member is configured to receive a drug for delivery through the lumen of the second elongate member. The stopper device is configured to control movement of the second elongate member within the first elongate member, thereby defining the retracted and extended positions of the second elongate member.

Implementations of the invention may include one or more of the following features. The stopper device can include a groove formed in the proximal end of the first elongate member and a retainer clip connected to the proximal end of the second elongate member, where the retainer clip is configured to engage the groove when the second elongate member is in the extended position. In another implementation, the stopper device includes a first finger grip included at the proximal end of the first elongate member and a second finger grip included at the proximal end of the second elongate member, where the second finger grip is configured to contact the first finger grip when the second elongate member is in the extended position.

The first elongate member can further include a second lumen extending therethrough, the second lumen including light fibers, and a third lumen extending therethrough, the third lumen including a micro-endoscope. A light post coupler can be coupled to the light fibers and configured to couple to a light source, and a camera adapter can be coupled to the micro-endoscope and configured to couple to a camera. A first connector can be coupled to the proximal end of the second elongate member and configured to couple to a drug source, and a second connector can be coupled to the proximal end of the second elongate member and configured to couple to a distension medium source. In one implementation, the drug delivered through the medical device is a local anesthetic.

In general, in another aspect, the invention features a system for drug delivery including a hysteroscope including a working channel and a medical device configured to position within the working channel of the hysteroscope. The medical device includes a first elongate member, a second elongate member and a stopper device. The first elongate member is configured for transcervical insertion into a uterine cavity and includes a proximal end, a distal end and a lumen extending therethrough. The second elongate member is positioned within the lumen of the first elongate member and includes a proximal end, a distal end and lumen therethrough. The second elongate member is positionable in a retracted or an extended position relative to the first elongate member. The distal end of the second elongate member is configured to extend beyond the distal end of the first elongate member and penetrate uterine tissue when in the extended position. The proximal end of the second elongate member is configured to receive a drug for delivery through the lumen of the second elongate member. The stopper device is configured to control movement of the second elongate member within the first elongate member, thereby defining the retracted and extended positions of the second elongate member.

Implementations of the invention may include one or more of the following features. The system may further include a drug source coupled to the proximal end of the second elongate member and/or a distension medium source coupled to the proximal end of the second elongate member. The stopper device can include a groove formed in the proximal end of the first elongate member and a retainer clip connected to the proximal end of the second elongate member, where the retainer clip is configured to engage the groove when the second elongate member is in the extended position. In another implementation, the stopper device can include a first finger grip included at the proximal end of the first elongate member and a second finger grip included at the proximal end of the second elongate member, where the second finger grip is configured to contact the first finger grip when the second elongate member is in the extended position.

The first elongate member can further include a second lumen extending therethrough, the second lumen including light fibers and/or a third lumen extending therethrough, the third lumen including a micro-endoscope. A light post coupler can be coupled to the light fibers and configured to couple to a light source. A camera adapter can be coupled to the micro-endoscope and configured to couple to a camera. The medical device may further include a first connector coupled to the proximal end of the second elongate member and configured to couple to a drug source and/or a second connector coupled to the proximal end of the second elongate member and configured to couple to a distension medium source. In one implementation, the drug delivered by the system is a local anesthetic.

In general, in another aspect, the invention features a method of delivering a drug to a uterus. The method includes transcervically positioning a delivery device within a uterine cavity until a distal end of the delivery device is near or contacting the fundus. The delivery device includes a second elongate member included in a lumen of a first elongate member and a stopper device configured to define a retracted position and an extended position of the second elongate member relative to the first elongate member. The second elongate member is translated within the lumen of the first elongate member toward the distal end of the delivery device and from a retracted position to an extended position. The tissue at or near the fundus is penetrated with a distal tip of the second elongate member, the second elongate member including a lumen filled with a drug. At least some of the drug is purged from the lumen of the second elongate member into the tissue at approximately the fundus.

Implementations of the invention can include one or more of the following features. The method can further include translating the second elongate member within the lumen of the first elongate member toward a proximal end of the delivery device and from the extended position to the retracted position, and withdrawing the delivery device from the uterine cavity.

The second elongate member can be coupled to a distension medium source, and the distension medium can be delivered to the uterine cavity through the lumen and distal tip of the second elongate member. Translating the second elongate member from a retracted position to an extended position can include engaging a retainer clip included a proximal end of the second elongate member with a locator included in a proximal end of the first elongate member. Translating the second elongate member from a retracted position to an extended position can include advancing a second finger grip included at a proximal end of the second elongate member toward and into contact with a first finger grip included at a proximal end of the first elongate member.

Transcervically positioning a delivery device within a uterine cavity can include transcervically positioning a hysteroscope within a uterine cavity, where the delivery device is included in a working channel of the hysteroscope. In one implementation, the drug delivered is a local anesthetic.

In general, in one aspect, the invention features a medical device for local anesthesia delivery. The medical device includes a first elongate member, a second elongate member and a stopper device. The first elongate member is configured for transcervical insertion into a uterine cavity and includes a proximal end, a distal end and a lumen extending therethrough. The second elongate member is positioned within the lumen of the first elongate member and includes a proximal end, a distal end and lumen therethrough. The second elongate member is positionable in a retracted or an extended position relative to the first elongate member. The distal end of the second elongate member is configured to extend beyond the distal end of the first elongate member and penetrate uterine tissue when in the extended position. The proximal end of the second elongate member is configured to receive a local anesthesia for delivery through the lumen of the second elongate member. The stopper device is configured to control movement of the second elongate member within the first elongate member, thereby defining the retracted and extended positions of the second elongate member.

Implementations of the invention may include one or more of the following features. The stopper device can include a groove formed in the proximal end of the first elongate member and a retainer clip connected to the proximal end of the second elongate member, where the retainer clip is configured to engage the groove when the second elongate member is in the extended position. In another implementation, the stopper device includes a first finger grip included at the proximal end of the first elongate member and a second finger grip included at the proximal end of the second elongate member, where the second finger grip is configured to contact the first finger grip when the second elongate member is in the extended position.

The first elongate member can further include a second lumen extending therethrough, the second lumen including light fibers, and a third lumen extending therethrough, the third lumen including a micro-endoscope. A light post coupler can be coupled to the light fibers and configured to couple to a light source, and a camera adapter can be coupled to the micro-endoscope and configured to couple to a camera. A first connector can be coupled to the proximal end of the second elongate member and configured to couple to a drug source, and a second connector can be coupled to the proximal end of the second elongate member and configured to couple to a distension medium source.

Implementations of the invention can realize one or more of the following advantages. A method or system for providing a controlled amount of local anesthesia to a particular location in uterine tissue is provided. Medical procedures that require anesthesia, yet are able to be performed in a physician's office using local anesthesia only, often can be performed without requiring the presence of an anesthesiologist. Additionally, the procedure can be performed without subjecting the patient to a general anesthesia, thereby avoiding possible side effects or complications associated therewith. A patient is able to recover from the procedure and be released from the medical office or hospital where the procedure was performed more quickly.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a top view of a drug delivery device.

FIG. 2 is a side view of the drug delivery device of FIG. 1.

FIG. 3 is an enlarged, cross-sectional view of the distal end of the drug delivery device of FIG. 1.

FIG. 4 is a side view of a portion of the proximal end of the drug delivery device of FIG. 1.

FIG. 6 is a top, partial cross-sectional view of an alternative implementation of a drug delivery device.

FIG. 7 is an enlarged, cross-sectional view of a distal end of the drug delivery device of FIG. 5.

Like reference symbols in the various drawings indicate like elements.

DETAILED DESCRIPTION

Figure 5:
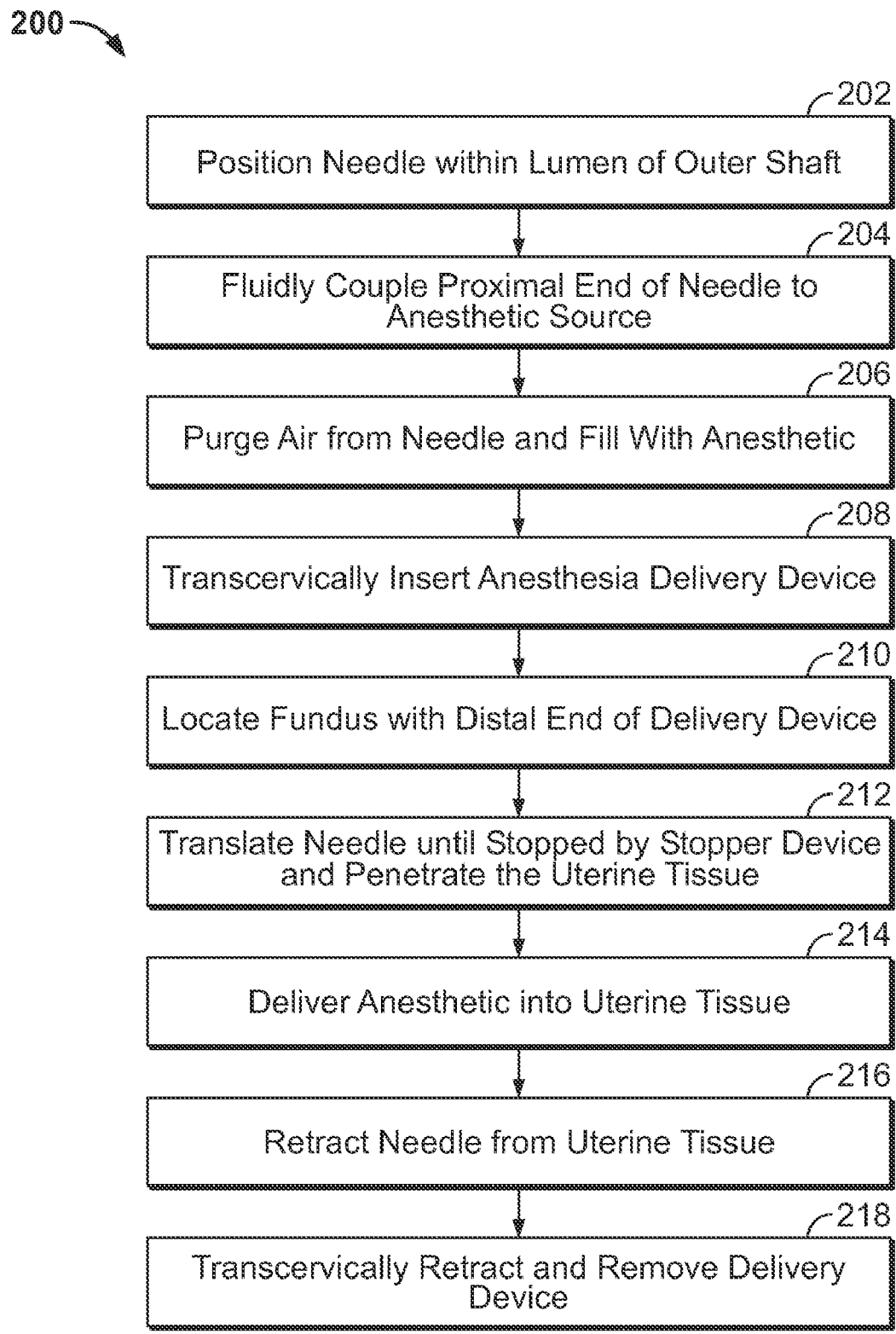
FIG. 5 is a flowchart showing a process for intrauterine delivery of a local anesthetic.

A medical device and technique for drug delivery to a uterus is described. A drug delivery device includes a first elongate member configured for transcervical insertion into a uterine cavity. The first elongate member includes a proximal end, a distal end and a lumen extending therethrough. A second elongate member is positioned within the lumen of the first elongate member and includes a proximal end, a distal end and lumen therethrough. The second elongate member is positionable in a retracted or an extended position. The distal end of the second elongate member is configured to extend beyond the distal end of the first elongate member and penetrate uterine tissue when in the extended position. The proximal end of the second elongate member extends from the proximal end of the first elongate member and is configured to receive a drug for delivery through the lumen of the second elongate member. The device further includes a stopper device configured to control movement of the second elongate member within the first elongate member thereby defining the retracted and extended positions of the second elongate member.

In one implementation, the drug delivery device can be used to deliver a local anesthesia. However, other drugs can be delivered into the uterine tissue, and a local anesthesia is merely one example. Any suitable drug, e.g., in a liquid or gel state, can be delivered either into the uterine cavity or the uterine tissue using the apparatus and processes described herein. For illustrative purposes, the apparatus and processes are described in reference to delivery of a local anesthetic, but it should be understood that this selection of drug is exemplary and not limiting.

Referring to FIG. 1, one implementation of a drug delivery device 100 is shown. The delivery device 100 includes a first elongate member, or outer shaft 102. The outer shaft 102 includes a distal end 104 and a proximal end 106. A lumen 108 (see FIG. 3) extends the length of the outer shaft 102. The outer shaft 102 can be configured to be straight or curved. In the curved implementation, the outer shaft 102 can be curved similarly to a conventional uterine sound to approximate the curvature of the uterine cavity. Near the proximal end 106 of the outer shaft 102 is a position locator 110. The locator 110 can be configured in any convenient manner, including, for example, a detent, groove or slot. In one implementation, the distal end 104 of the outer shaft 102 can be configured to prevent damage to the uterine tissue during tactile placement, for example, the distal end 104 can be rounded.

A second elongate member, or needle 112, is positioned coaxially within the lumen 108 of the outer shaft 102. The needle 112 includes a distal end 114 configured to penetrate uterine tissue, e.g., tissue at the fundus of the uterus. The needle 112 further includes a proximal end 116 that protrudes from the proximal end of the outer shaft 102. In this implementation, the proximal end 116 includes a leur connector 118. The leur connector 118 can couple to a drug-filled syringe to fill the lumen of the needle 112 with the drug, e.g., an anesthetic. Other connectors can be used in place of the leur connector 118, which is one exemplary configuration. Alternatively, the proximal end 116 of the needle 112 can include a drug source, e.g., can include an integrated syringe.

A stopper device is included in the proximal region of the needle 112. The stopper device in the implementation shown is a retainer clip 120 that can engage with a slot-type locator 110 located on the proximal end 106 of the outer shaft 102. However, other configurations of stopper device can be used, and the configuration shown is exemplary. When the needle 112 is in the retracted position, the retainer clip 120 is in a position A. When the needle 112 is advanced through the lumen 108 of the outer shaft 102 into the extended position, the retainer clip 120 is in a position B. Position B of the retainer clip 120 corresponds to the retainer clip 120 engaging the locator 110, which prevents the retainer clip, and therefore the needle 112, from any further advancement. The distance the distal end 114 of the needle 112 translates into the fundus tissue can thereby be controlled. That is, the difference in distance between position A (retracted position; FIGS. 2 and 3) and position B (extended position; FIGS. 3 and 4), which is shown in FIGS. 2 and 3 as length 122, can be set by a physician to control how far the distal end 114 of the needle 112 extends from the distal end 104 of the outer shaft 102. For example, the distal end 114 may extend in the range of approximately 1 to 10 mm, or approximately 5 mm, depending on the application.

In one implementation, position A of the retainer clip 120 is adjustable by a user to adjust the travel distance of the retainer clip 120 and therefore adjust the extended position of the distal end of the needle 112. In another implementation, position A of the retainer clip 120 is fixed, thereby providing a fixed extended position of the distal end of the needle 112.

The delivery device 100 can be inserted into the uterine cavity along the mid-plane of the uterus, or can be turned to either side to come into contact with the regions of the cornua. The distance the distal end 114 of the needle 112 protrudes from the distal end of outer shaft 102 can be adjusted as a function of the location of the desired injection. For example, the extension distance for a drug injection at the midline of the fundus may be set deeper, e.g., approximately 10 mm, than the extension distance set for injection into the cornua, e.g., approximately 5 mm.

Referring to FIG. 5, a flowchart is shown illustrating a process 200 for using a drug delivery device to deliver a local anesthetic to the fundus tissue. For illustrative purposes the process shall be described in reference to the implementation of the delivery device 100 shown in FIG. 1. However, it should be understood that other implementations of the delivery device can be used to carry out the process, and that the steps of the process can be carried out in a different sequence, while still achieving the desired results.

The needle 112 is positioned within the lumen 108 of the outer shaft 102 (step 202). The proximal end 116 of the needle is fluidly coupled to a source of anesthetic (step 204). For example, in the implementation being described, an anesthetic filled syringe is connected to the leur connector 118. Any fluid or gas contained within the needle 112 (e.g., air) is purged and substantially the entire lumen of the needle 112 is filled with the anesthetic (step 206). The drug delivery device 100 is transcervically inserted into the uterine cavity (step 208) and the fundus is located with the distal end 104 of the outer shaft 102 (step 210). A physician or other medical person using the device can detect the outer shaft 102 has reached the fundus by tactile feedback. The needle 112 is moved within the lumen 108 of the outer shaft 102 until the needle 112 can move no further, due to the stopper device, e.g., the retaining clip 120, ceasing translation of the needle. The distal end 114 of the needle—during the movement—pierces and enters the tissue at the fundus of the uterus (step 212). The desired amount of anesthetic is delivered into the tissue, e.g., by pushing the plunger of the syringe attached to the needle 112 (step 214). The distal end 114 of the needle is then retracted and withdrawn from the tissue (step 216). The delivery device 100 is then transcervically retracted and removed from the uterine cavity and the patient's body (step 218). The above procedure is described in the context of delivering a local anesthetic to uterine tissue, however, as previously mentioned, a local anesthetic is just one example of a drug that can be delivered using the device and procedure described herein.

Other implementations of the delivery device are possible. Referring to FIG. 6, an alternative implementation of a delivery device 300 is shown. The delivery device 300 is configured as a catheter with a diameter 302 sufficiently small so as to be compatible with the working channel of a hysteroscope. The delivery device 300 can be inserted into a uterine cavity either alone or can be used in conjunction with a conventional hysteroscope for use under direct visualization. The delivery device 300, having a distal end 304 and a proximal end 306, includes an external sheath 308 extending between the distal and proximal ends, with a first finger grip 310 located at the proximal end 306. The external sheath 308 includes a lumen 311 extending the length of the external sheath 308. A needle 312 is positioned within the lumen 311. The needle 312 includes a distal tip 314 configured to penetrate tissue, and a proximal end 316 with a second finger grip 318 attached. The needle 312 includes a lumen 320 extending the length of the needle 312, including extending through the second finger grip 318. The lumen 320 is fluidly coupled to an anesthetic source. In this implementation, tubing 322 and a standard leur connector 324 included at the proximal end 316 of the needle 312 fluidly couple the lumen 320 to an anesthetic filled syringe that can be connected to the leur connector 324.

The first finger grip 310 attached to the external sheath 308 and the second finger grip 318 at the proximal end of the needle 312, together form a stopper device. In use, the delivery device 300 can be inserted into the uterine cavity and the distal end 304 of the external sheath 308 advanced to the fundus. A distance 326 between the first finger grip 310 and the second finger grip 318 corresponds to a controlled travel distance of the needle 312. Referring to FIG. 7, an enlarged view of the distal region of the needle 312 is shown. The distal tip 314 of the needle 312 travels the same distance 326 as the second finger grip 318 travels to come into contact with the first finger grip 310. Therefore, the protrusion of the distal tip 314 from the distal end 304 of the external sheath 308 is controllable to a predetermined distance. As such, the penetration of the distal tip 314 into the uterine tissue is also controllable.

Figure 8:
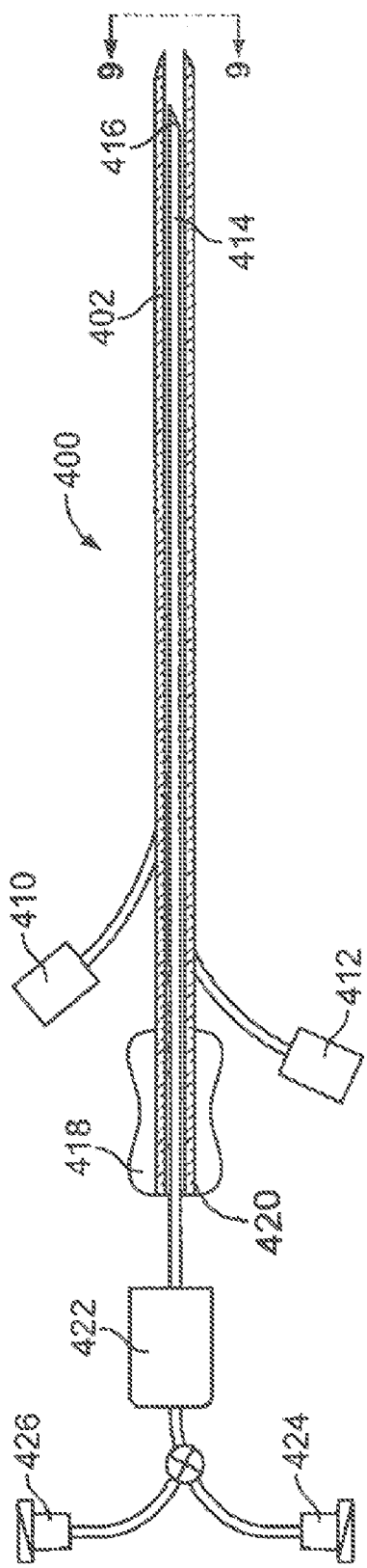
FIG. 8 is a top, partial cross-sectional view of an alternative implementation of a drug delivery device.
Figure 9:
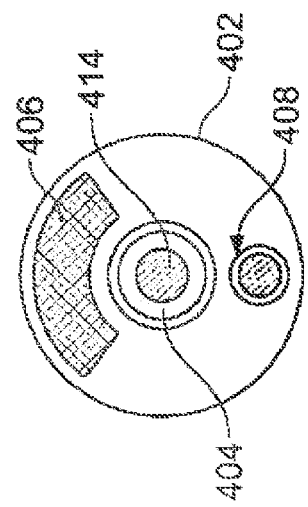
FIG. 9 is an end view of a distal end of the alternative implementation of the drug delivery device of FIG. 8.

Referring now to FIG. 8, another implementation of a delivery device 400 is shown. The delivery device 400 is similar to the implementation shown in FIG. 6, but includes a triple lumen sheath 402. This implementation is configured for direct visualization during device and needle placement. FIG. 9 shows an end view of the delivery device 400. The sheath 402 includes a central lumen 404 and additional lumens 406 and 408. Lumen 406 includes light fibers and lumen 408 includes a micro-endoscope. A light post coupler 410 is coupled to the light fibers within lumen 406 and is configured to connect to a light cable, providing a light source to the fibers. A camera adapter 412 is coupled to the micro-endoscope included in lumen 408 and is configured to connect to a digital camera.

The delivery device 400 includes a needle 414 positioned coaxially within the central lumen 404 and including a distal tip 416 configured to pierce uterine tissue. A first finger grip 418 is included at the proximal end 420 of the triple lumen sheath 402. A second finger grip 422 is included at the proximal end of the needle 414. As explained above in reference to the implementation shown in FIG. 6, the first and second finger grips 418, 422 together form a stopper device and can be used to control the distance the distal tip 416 of the needle 414 extends from the distal end of the triple lumen sheath 402. Other configurations of stopper device can be used, including, for example, the configuration shown in FIG. 1 (i.e., a retainer clip and locator).

A standard leur connector 424 is coupled to the proximal end of the needle 414 and configured to connect to a drug source, e.g., a syringe. Other configurations of connector can be used. In the implementation shown, a second standard leur connector 426 is also included and coupled to the proximal end of the needle 414. The second leur connector 426 can be fluidly coupled to a distension medium, for example, a saline solution. Some uses of the delivery device 400 may require the uterine cavity be distended prior to or after delivery of the drug. A distension medium can be delivered into the uterine cavity using the same needle 414 as used to delivery the drug into the uterine tissue.

In another implementation, the second leur connector can be included in a delivery device, such as that shown in FIG. 1 or 6, including a single lumen in the external sheath. Other configurations are possible, including different combinations of configurations of stopper device, numbers of lumens, and numbers of leur connectors and types of connectors. The implementations described are exemplary.

In any of the implementations of the delivery device, including the delivery devices 100, 300 and 400 discussed above, the first elongate member (i.e., the outer shaft, external sheath or triple lumen sheath) can be formed using any suitable material, including for example, an extruded thermoplastic elastomer. The second elongate member (i.e., the needle) can be formed from any suitable material, including for example, a stainless steel tubing hypotube.

A number of embodiments of the invention have been described. Nevertheless, it will be understood that various modifications may be made without departing from the spirit and scope of the invention. For example, the steps shown in FIG. 5 can be performed in a different order and still achieve desirous results. Additionally, as noted above, the delivery device can be used to deliver drugs other than an anesthetic to the uterine cavity or uterine tissue, and the invention described herein is not limited to delivery of a local anesthetic. Accordingly, other embodiments are within the scope of the following claims.

What is claimed is:

1. A drug delivery device adapted for insertion into a working channel of a hysteroscope comprising:
   a first elongate member configured for transcervical insertion into a uterine cavity, the first elongate member including a proximal end, a distal end and a first lumen, a second lumen and a third lumen extending therethrough between the proximal and distal ends, wherein the second lumen includes light fibers and the third lumen includes a micro-endoscope;
   a light post coupler coupled to the light fibers and configured to couple to a light source;
   a camera adapter coupled to the micro-endoscope and configured to couple to a camera;
   a second elongate member positioned within the first lumen of the first elongate member and including a proximal end, a distal end and a lumen therethrough, where:
      the second elongate member is positionable in a retracted or an extended position relative to the first elongate member;
      the distal end of the second elongate member is configured to extend beyond the distal end of the first elongate member and pierce uterine tissue when in the extended position;
      the proximal end of the second elongate member is configured to receive a drug for delivery through the lumen of the second elongate member; and a stopper device configured to control movement of the second elongate member within the first elongate member thereby defining the retracted and extended positions of the second elongate member, the stopper device including a first gripping member fixedly secured to the proximal end of the first elongate member and a second gripping member fixedly secured to the proximal end of the second elongate member, where the second gripping member is configured to abut the first gripping member in a non-engaging fashion when the second elongate member is in the extended position.

2. The device of claim 1, further comprising:
a first connector coupled to the proximal end of the second elongate member and configured to couple to a drug source; and
a second connector coupled to the proximal end of the second elongate member and configured to couple to a distension medium source.

3. The device of claim 2, wherein at least one of the first and second connectors is a leur connector.

4. The device of claim 1, wherein the drug is a local anesthetic.

5. The device of claim 1, wherein the first elongate member is curved.

6. The device of claim 1, wherein the distal end of the first elongate member is rounded.

7. The device of claim 1, wherein the second elongate member is a needle.

8. The device of claim 1, wherein the distal end of the second elongate member is configured to extend approximately 1 to 10 mm beyond the distal end of the first elongate member.

9. The device of claim 1, further comprising:
a drug source coupled to the proximal end of the second elongate member.

10. The device of claim 9, further comprising:
a distension medium source coupled to the proximal end of the second elongate member.

* * * * *